United States Patent [19]
Vincent

[11] 4,024,861
[45] May 24, 1977

[54] SPINAL SUPPORT

[76] Inventor: David Conway Vincent, 33 Driftwood Drive, Brantford, Ontario, Canada, N3R 3K2

[22] Filed: Apr. 30, 1976

[21] Appl. No.: 681,774

[30] Foreign Application Priority Data

May 13, 1975 Canada .............................. 226766

[52] U.S. Cl. .............................. 128/87 R; 128/134
[51] Int. Cl.² ............................................ A61F 5/04
[58] Field of Search ....... 128/134, 87, 89, DIG. 20, 128/78

[56] References Cited

UNITED STATES PATENTS

| 3,217,333 | 11/1965 | Sweet et al. | 128/DIG. 20 |
| 3,232,289 | 2/1966 | Zimmerman | 128/87 R |
| 3,242,923 | 3/1966 | Jacoby | 128/DIG. 20 |
| 3,620,211 | 11/1971 | Goodell et al. | 128/89 |
| 3,737,923 | 6/1973 | Prolo | 128/78 |
| 3,762,404 | 10/1973 | Sakita | 128/78 |
| 3,974,827 | 8/1976 | Bodeen | 128/DIG. 20 |

FOREIGN PATENTS OR APPLICATIONS

| 1,221,134 | 1/1960 | France | 128/DIG. 20 |
| 1,015,989 | 8/1952 | France | 128/DIG. 20 |

*Primary Examiner*—Lawrence W. Trapp
*Attorney, Agent, or Firm*—Otto John Munz

[57] ABSTRACT

Spinal support, particularly for use in first aid treatment of victims of spinal injuries. The support is of the type of an inflatable bag to which the victim is secured to immobilize his or her spine during transportation to hospital or the like. The outer shell of the bag has longitudinal reinforcement ribs to facilitate the handling of the injured with the support attached.

16 Claims, 9 Drawing Figures

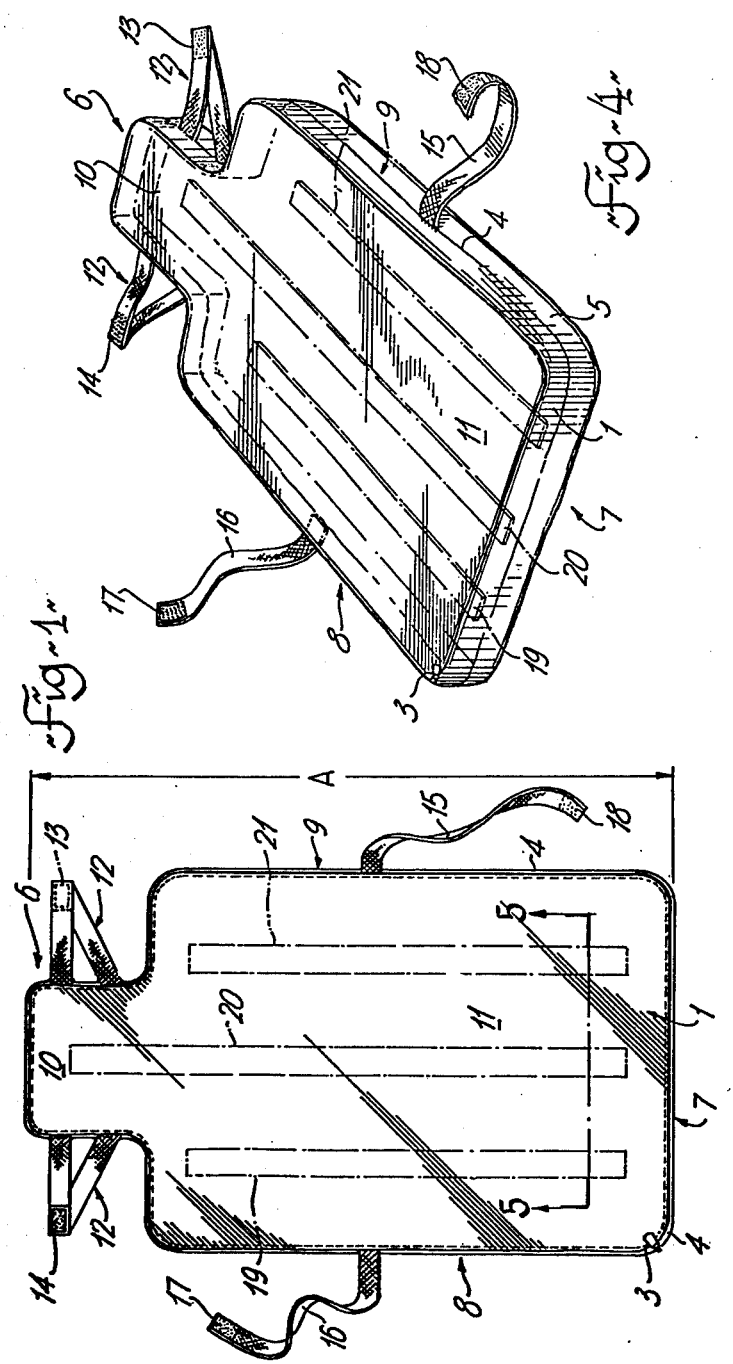

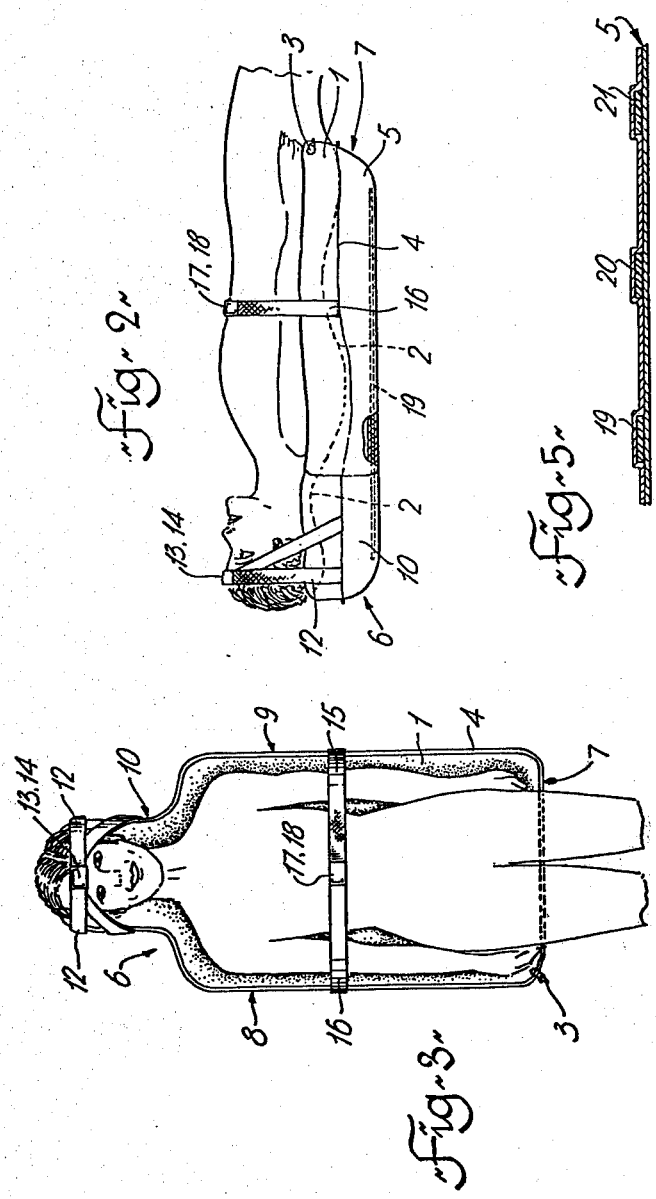

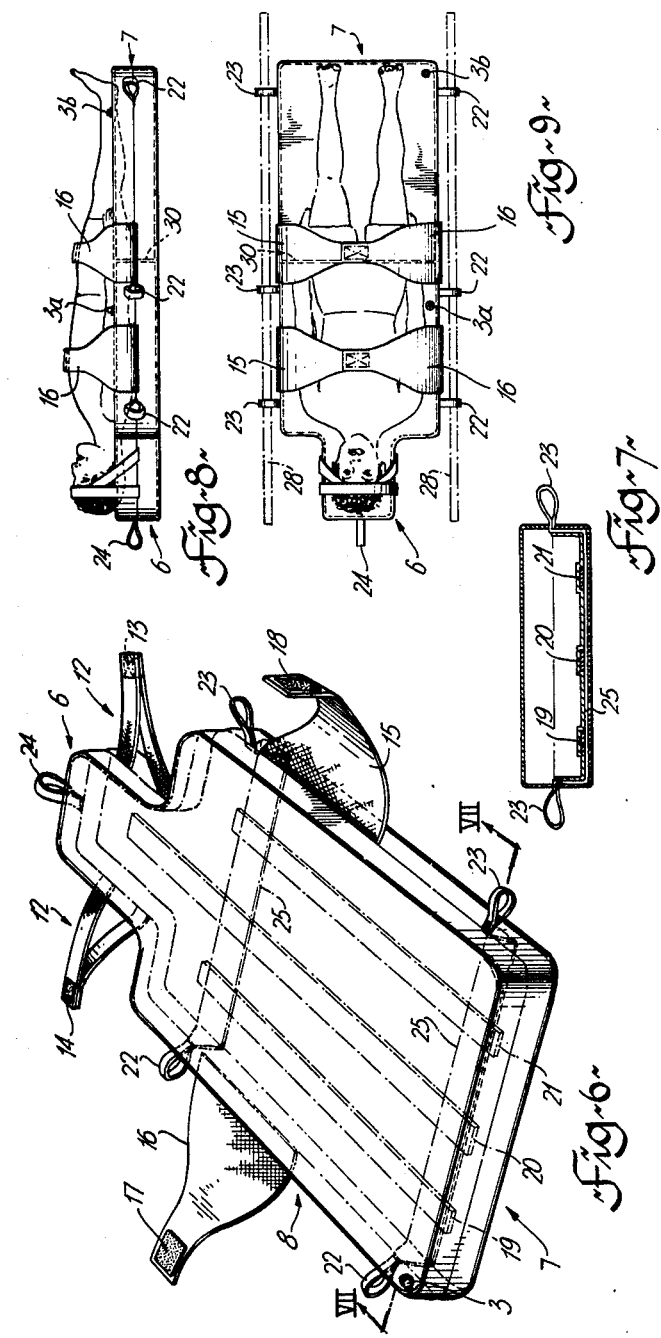

SPINAL SUPPORT

The present invention relates to a spinal support for use in first aid treatment of the victim of a spinal injury, particularly, but not limited to, the victim of a sphinal injury suffered in sports such as diving, water or snow skiing, football or the like, in car accidents, etc.

The primary purpose of spinal support of this type is to provide first aid when spinal injury is suspected, by immobilizing the spinal column of the injured as any movement of the injured spine can cause total paralysis of the injured.

The presently known and used support of this type, introduced about 25 years ago (durning the Korean war), is so-called spine board made from ¾ inch marine plywood and having dimensions of about 72 inches by 20 inches. Three straps are secured to the board for fastening the victim to the board. When a spinal injury is suspected, the board is manoeuvered under the floating victim and the straps are applied. The region about the head and neck is then padded in a way that prevents the movement of these. The victim is now ready for transport.

The spine board has several disadvantages. Its large size makes it clumsy to use in the water. If the rescue operation is effected with anything less than perfect co-ordination, the vicitm will suffer further grief. The use of rolled towels or sandbags to pad the neck and head regions creates another major area for mistake. It takes considerable skill to position these items properly without causing the head and neck to move. The straps with this board are loosely attached through slots. This casual arrangement can create problems such as the strap being out of the slot which makes the process less efficient. The natural buoyancy of the board may cause it to move unexpectedly if someone loses their concentration even for a second. The operation of this device requires a minimum of three people to be effective with five being the recommended number. The disadvantage here is that the more people involved the harder it is to organize and co-ordinate the process. Also, it is often hard to find that many people with the presence of mind needed to be effective in the emergency situation.

The present invention reduces the above drawbacks by providing a spinal support comprising, in combination, a back support of the type of an inflatable bag. The bag has an "upper shell", (the term "upper shell" meaning the portion of the bag wall that actually supports the back of the victim with the bag in inflated condition). The bag further comprises a "bottom shell" of generally the same shape as the upper shell, the term "bottom shell" designating, basically, the portion of the bag which forms the outer side and bottom surface of the bag as applied. The term "bottom shell" thus actually designates the outer wall portion of the bag as applied to the victim. It will be appreciated that the bag can either be a more or less unitary product wherein both the upper shell and the bottom shell are formed by a single piece of impermeable material, or the two shells can be made of two or more separate sheets welded together by a peripheral seam or the like. It will thus be appreciated that the terms "upper shell" and "bottom shell" are merely intended to refer to the portions of bag that are adjacent the victim's body (upper shell) and remote from same (bottom shell) with cushioning air inbetween, the two portions having distinctly different effect during the use of the support; while the upper shell actually supports the back of the victim, the bottom shell actually provides the outside surface of the applied support. The bag has a front end, a rear end and two sides. A head portion of the said bag is provided by an extension of the front end and unitary with same, the extension being located centrally and being arranged to support the head of the victim. The width of the head portion is smaller than that of the remaining portion of the bag. The overall distance between the front end of the head portion and the rear end of the bag is about 115 centimeters. The distance can also be greater and can be referred to generally as being a distance greater than at least the distance between the top of the head and the lower end of the spine of the victim. Head strap means are arranged at the sides of the head portion. Such means is adapted to secure the head of the victim to the head portion. Body strap means are arranged at the sides of the remaining portion of the bag for securing at least the chest of the victim to the bag. Longitudinal reinforcement means are secured to the outer or bottom shell to provide same with rigidity in longitudinal direction thereof. At least one of the reinforcement means is a unitary, elongated, reinforcement member extending centrally of the outer or bottom shell and having the length substantially corresponding to the distance between the front end of the head portion and the rear end of the bag. The bag is mouth inflatable.

The overall length of the bag can also be made greater than the height of the victim. The length of about 230 cm normally meets such requirement as a man's height over 230 cm is very unusual.

The shell portions of the bag are preferably made from a transparent material to facilitate preliminary visual examination of the victim without the need for removing the support. The invention will now be described in greater detail with reference to the embodiments shown in the accompanying drawings in which:

FIG. 1 is a schematic plan view of an unrolled, deflated support according to one embodiment of the present invention;

FIG. 2 is a schematic side view of the support in inflated state and applied to the victim;

FIG. 3 is a plan view of the support;

FIG. 4 is a perspective view of the support of FIG. 1 in inflated state; and

FIG. 5 is a section 5—5 of FIG. 1.

FIG. 6 is a perspective view similar to FIG. 4 but showing a further embodiment of the present invention;

FIG. 7 is a section VII—VII of FIG. 6;

FIG. 8 is a side view similar to FIG. 2 but showing a still further embodiment of the present invention; and FIG. 9 is a top view similar to FIG. 3 but showing a yet further embodiment of the present invention.

In the drawings the corresponding parts are referred to with the same reference numerals even when the Figures show different embodiments of the invention.

With reference to FIG. 1, it will be seen that a back support is shown which is of the type of an inflatable bag including an upper shell 1. It will be appreciated that the upper shell 1 comes into contact to support the back 2 of the victim upon mouth inflation of the bag through a valve 3.

The upper shell 1 is joined at a peripheral seam 4 (not shown in FIGS. 2 and 3) to a bottom shell 5 which, in FIG. 1 is coincident with the upper shell 1.

The upper shell 1 and the bottom shell 5 thus form a bag made from PVC sheets of suitable strength. As best seen from FIG. 1, the bag has front end 6, rear end 7 and two sides 8, 9.

The bag forms, at its front end 6, a central, generally square-shaped extension which can also be referred to as a head portion 10. The head portion 10 is located centrally of the bag and, as seen in FIGS. 2 and 3, is arranged to support the head of the victim. The width of the head portion 10 is smaller than that of the remaining or body portion 11 of the bag.

In the shown embodiment, the overall distance A between the front end of the head portion and the rear end of the bag is slightly greater than the distance between the top of the victim's head and the lower end of his or her spine. Normally, such condition is met if the distance A is approximately 110 centimeters. The width of the body portion is sufficient to partly envelope the body of the victim. Normally the width of about 100 centimeters will meet this requirement.

Fixedly secured to the sides of the head portion 10 are head straps 12 arranged for securing the victim's head to the support. The straps are secured to the head portion by welding or the like in proximity to the peripheral seam 4. As best seen from FIG. 1, each of straps 12 is a V-shaped structure the apex of one of such structure being provided with one half 13 of a "Velcro" fastener, the other structure being provided with the other half 14 of the fastener. The fasteners of the above type are well known and do not have to be described in greater detail. The spread-apart ends of the straps 12 are secured to the head portion 10 as mentioned above.

Similarly, secured to the sides 8, 9 are straps 15, 16 for securing the chest of the victim to the support. The straps 15, 16 are also provided with fastener halves 17, 18 as referred to above.

The bottom shell 5 is made of double-walled PVC sheet with 3 elongated, relatively rigid, flat ribs 19, 20, 21 interposed between the two walls of the bottom shell 5 and secured to same by welding. It will be seen from FIG. 1 that the central rib 20 extends with its front end close to the front end of the head portion 10, while the side ribs 19, 21 terminate at the front end of the body portion 11. It will be appreciated that the ribs 19, 20, 21 provide the bottom shell 5 with rigidity required during the handling of the victim with the support applied.

The shells 1, 5 are made of transparent material to facilitate visual examination of the victim with the support applied.

Turning now to FIGS. 6 and 7, a further embodiment of the invention is shown. This particular embodiment is different from the above disclosed type of the device of this invention in that it comprises holder means of the type of flexible hand loops or hand straps 22, 23 which are fixedly secured to the sides of the bag. The straps 22, 23 are used in comfortable carrying of the bag with the victim secured to same. As best seen from the section of FIG. 7, each of the pairs of straps 22, 23 is unitary with a web 25 extending between the opposite sides of the bag and fixedly secured to the bottom shell of same, by embedding the web 25 so that it is located beneath the ribs 19, 20, 21. In general terms, the web 25 is located adjacent those surfaces of ribs 19, 20, 21 which are remote from the inside of the bag.

It will also be observed from FIG. 6 that the straps 15, 16 are of a shape different from that of FIG. 4. Each of straps 15, 16 in FIG. 6 has a first end fixedly secured to the respective side of the bag and a second end carrying the fastener portions 17, 18. The width of each of straps 15, 16 increases from the free or second end towards the first end secured to the bag. This assists in a more comfortable securing of the victim to the bag, as the securing is effected over a larger area of the victim's body.

FIG. 8 shows a still further embodiment of the present invention. This particular embodiment is a bag whose overall length is approximately 230 centimeters. In other words, the overall length of the bag is in excess of normal human height. Consequently, the bag is arranged to support the entire body of the victim, inclusive his or her legs. Two pairs of fastening straps 15, 16 are used in this embodiment. The bag is divided into two separate compartments by way of a divider wall 30. The wall 30 is a flexible membrane fixed to the respective portions of the bag in air tight fashion. Consequently, the wall 30 divides the inside of the bag into two entirely separate compartments which can be inflated independent on each other through valves 3a, 3b. The wall 30 extends generally parallel with the rear end 7 of the bag, as best seen from FIG. 9. The spacing of the divider wall 30 from the front end 6 is roughly the same as the distance between the front end 6 and the rear end 7 in FIG. 6 or FIG. 4, i.e. approximately 115 centimeters.

The embodiment of FIG. 9 is a further improvement of the present invention, wherein the hand straps 22, 23 are replaced by somewhat smaller loops 22, 23 through which can pass poles 26, 28, so that the overall support can be carried around in a fashion similar to the carrying of a regular stretcher. The poles 26, 28, of course, must be of sufficient length to secure a comforable and safe handling of the support. In other words, they must be longer than the overall length of the bag as measured from its front to the rear. Those skilled in the art will, of course, appreciate that the support of, say, FIG. 6 can also be combined with the carrying poles 26, 28. Moreover, if desired, the poles 26, 28 may be secured to the side of the bag in a fixed manner rather than in the releasable fashion as shown in FIG. 9.

The spinal support or jacket of the present invention is applied in inflated state. Mouth-inflation is a preferred, but not the only way of inflating the support as over-inflating of the bag would make the surface of the upper shell too hard and thus unsuitable for the above purpose.

The advantages of the present invention over the presently used spine boards are numerous. The fact that it is an inclusive unit is a very significant advance. This removes the need for extraneous material such as padding or towels, the latter being the most common implement now used to immobilize the head of the victim. This helps to minimize the probability of human error previously associated with the use of the towels or other forms of padding. It is light and very portable. It facilitates its application because of its smaller size. It rolls up when deflated and this makes storage easy. It conforms to the natural curves of the spine when the inflated. This puts the injured spine in the desired position immediately without any fiddling needed, to prevent any further aggravation of the injury. The straps are permanently attached to the body of the support and are easy to use. They attach the jacket snugly to the body without interfering with the breathing mechanism. The jacket is more comfortable than a board which is important in the treatment of shock. The support is transparent, which is advantageous in that the jacket can remain on the victim while his injuries are being properly diagnosed. The board is more buoyant than wood when inflated, thereby insuring that the breathing apparatus of the victim is out of the water. The jacket can be made complimentary to any ambulance system so it need not be removed until the victim is safely in the hospital. The support is simple to use, reduces the human error factor as much as possible and is safer in the hands of the inexperienced. It also takes less people to operate it effectively. It the victim is breathing on his or her own, one person could apply the support in emergency. It only needs two people to be effectively used in most cases, as opposed to three to five people required for the known spinal board.

It will be appreciated that the embodiments of the invention as described can be further modified to a greater or lesser degree without departing from the scope of the present invention as defined in the accompanying claims.

The embodiments of the invention in which an exclusive property or privilege is claimed are defined as follows:

1. Spinal support comprising, in combination:
   a. a back support of the type of an inflatable bag comprising an inner, body supporting shell portion and an outer shell portion, said shell portions being generally identical in size and shape and having each a head portion and a body portion defining a head portion a head portion and a body portion of said bag;
   b. first securing means arranged for securing said head portion of the bag to the head of a victim;
   c. second securing means arranged for securing said body portion of the bag to the body of said victim;
   d. longitudinal reinforcement means secured to said outer shell, said reinforcement means being adapted to provide at least a portion of said outer shell with rigidity in longitudinal direction thereof.

2. Spinal support comprising, in combination:
   a. a support of the type of an inflatable bag, said bag having upper shell adapted to effectively support the back of a patient upon inflation of said bag; said bag further comprising;
   b. a bottom shell of substantially the same size and shape as the upper shell;
   c. said upper shell and said bottom shell being secured to each other about their periphery to define said bag, said bag thus having a front end, a rear end and two sides;
   d. a head portion of the said back being provided by an extension of said front end and being unitary with same, said extension being located centrally and being arranged to support the head of a victim, the width of said head portion being smaller than that of the remaining portion of the bag;
   e. the overall distance between the front end of the head portion and the rear end of the bag being greater than at least the distance between the top of the head and the lower end of the spine of said victim;
   f. head securing means arranged to said head portion and adapted to secure the head of said victim to said head portion;
   g. body securing means arranged at the remaining portion of the bag for securing at least the chest of the victim to the bag;
   h. longitudinal reinforcement means secured to said outer shell to provide at least a portion of same with rigidity in longitudinal direction thereof, at least one of said reinforcement means being a unitary, elongated reinforcement member extending centrally of said outer shell and having the length substantially corresponding to the distance between the front end of the head portion and the rear end of the bag.

3. Support as claimed in claim 2, wherein the overall distance between the front end of the head portion and said rear end of the bag is greater than the height of said victim.

4. Support as claimed in claim 3, further comprising a flexible divider wall extending transversely of said bag and dividing the interior of said bag in air-tight fashion into two separate compartments; and value means for separately inflating each of said compartments.

5. Support as claimed in claim 4, wherein said dividing wall is located such that said two compartments are of a generally identical volume; said divider wall extending in a direction generally transversely of said bag and being spaced from said front end of the head portion at adistance greater than the distance between the top of the head and the lower end of the spine of said victim.

6. Support as claimed in claim 1, further comprising means for mouth inflation of said bag.

7. Support as claimed in claim 1, wherein said means for securing the head of the victim is a pair of generally V-shaped straps having apex portions which are provided with a fastener for fastening said straps to one another opposite, spread apart ends of said straps being secured to their respective sides of the head portion.

8. Support as claimed in claim 1, wherein said reinforcement means are narrow, unitary, generally rigid ribs spaced from each other and embedded in said outer or bottom shell portion and disposed longitudinally thereof, at least one of the ribs being a central rib extending with one of its ends to the front end of the head portion, to support same the opposite end of said central rib being located in proximity of said rear end of the bag, at least one additional rib being arranged to each side of said central rib, one end of each of said additional ribs terminating at said rear end of the bag, the opposite end of same terminating at the front end of the body portion spaced from the head portion.

9. Support as claimed in claim 1, wherein said shell portions are made from a transparent material whereby visual examination of the victim with the support applied is facilitated.

10. Support as claimed in claim 2, further comprising holder means fixedly secured to said sides of the bag for facilitating the carrying of said support.

11. Support as claimed in claim 10, wherein said holder means are hand strap loops unitary with a web extending between the opposite sides of the bag and fixedly secured to said bottom shell portion thereof.

12. Support as claimed in claim 11, wherein said web is located adjacent to that surface of said reinforcement means which is remote from the inside of said bag.

13. Support as claimed in claim 2, wherein said body securing means includes a pair of straps, each having a first end fixedly secured near the respective side of the bag; a second end of each of said straps being adapted to be releasably secured to the second end of the other strap of said pair, the width of each of said straps increasing in the direction from said first end to said second end thereof.

14. Support as claimed in claim 10, wherein said holder means is means for securing to each side of said bag two elongated rod-like members whose length is in excess of the distance between said front and said rear ends of the bag.

15. Support as claimed in claim 14, wherein said holder means is a plurality of flexible strap loops fixedly secured to said bag near the sides thereof, the straps being arranged to slidably receive said rod-like members.

16. Support as claimed in claim 10, wherein said holder means includes a plurality of strap loops secured to the sides of said bag; and two rod-like, generally rigid pole members whose length, is in excess of the overall length of the bag, said strap loops being disposed in two rows, each row being arranged along one side of the bag, whereby each of said pole members can be inserted into the loops of one side to provide a stretcher-like structure to facilitate the carrying of said victim.

* * * * *